United States Patent
Montgomery et al.

(10) Patent No.: US 6,385,560 B1
(45) Date of Patent: May 7, 2002

(54) DIAGNOSIS OF REPETITIVE QUALITY FAULTS

(75) Inventors: Kerry A. Montgomery, Lake Oswego; Debra J. Schroeder, Beavercreek, both of OR (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/390,602

(22) Filed: Sep. 3, 1999

(51) Int. Cl.$^7$ .............................................. G01N 21/89
(52) U.S. Cl. ...................... 702/183; 702/182; 702/185; 702/81; 702/84; 702/33
(58) Field of Search .............................. 702/33, 35, 36, 702/81–84, 108, 127, 163, 183, 182, 184, 185, FOR 123, FOR 124, FOR 125, FOR 134, FOR 135, FOR 137, FOR 170, FOR 171; 399/9, 15; 347/19, 104, 105, 107; 346/33 MC

(56) References Cited

U.S. PATENT DOCUMENTS

| 3,893,175 A | * | 7/1975 | Solomon ........................ 360/6 |
| 4,062,061 A | * | 12/1977 | Batchelor et al. ........... 364/900 |
| 4,163,897 A | * | 8/1979 | Hubbard et al. ......... 235/92 SB |
| 4,310,844 A | * | 1/1982 | Imamoto ..................... 346/1.1 |
| 4,390,872 A | * | 6/1983 | Murakami et al. ........... 340/679 |
| 4,739,366 A | * | 4/1988 | Braswell et al. ......... 355/14 SH |
| 4,855,754 A | * | 8/1989 | Tanaka et al. ................. 346/17 |
| 4,937,626 A | * | 6/1990 | Kohtani et al. .............. 355/245 |
| 4,937,664 A | * | 6/1990 | Chiku et al. ................... 358/75 |
| 5,175,570 A | * | 12/1992 | Haneda et al. ............... 346/160 |
| 5,311,255 A | * | 5/1994 | Josephson .................... 355/206 |
| 5,381,167 A | * | 1/1995 | Fujii et al. ................... 346/157 |
| 5,532,789 A | * | 7/1996 | Yaginuma et al. ........... 355/202 |

* cited by examiner

*Primary Examiner*—Marc S. Hoff
*Assistant Examiner*—Carol S Tsai

(57) ABSTRACT

A method of improving diagnosis of repetitive quality faults appearing in prints from a printer having rotating elements uses an internal test page that has a lead edge, a trail edge, a ruled margin, a reference mark at the start of the ruled margin adjacent the lead edge, and labeled characteristic marks spaced from the reference mark according to the circumference of the various rotating elements. A user prints the test page and places it atop a print that has a repetitive quality fault, with the reference mark aligned with a first occurrence of the fault. The label of the characteristic mark adjacent a second occurrence of the fault identifies the rotating element probably causing the fault which needs to be replaced.

2 Claims, 1 Drawing Sheet

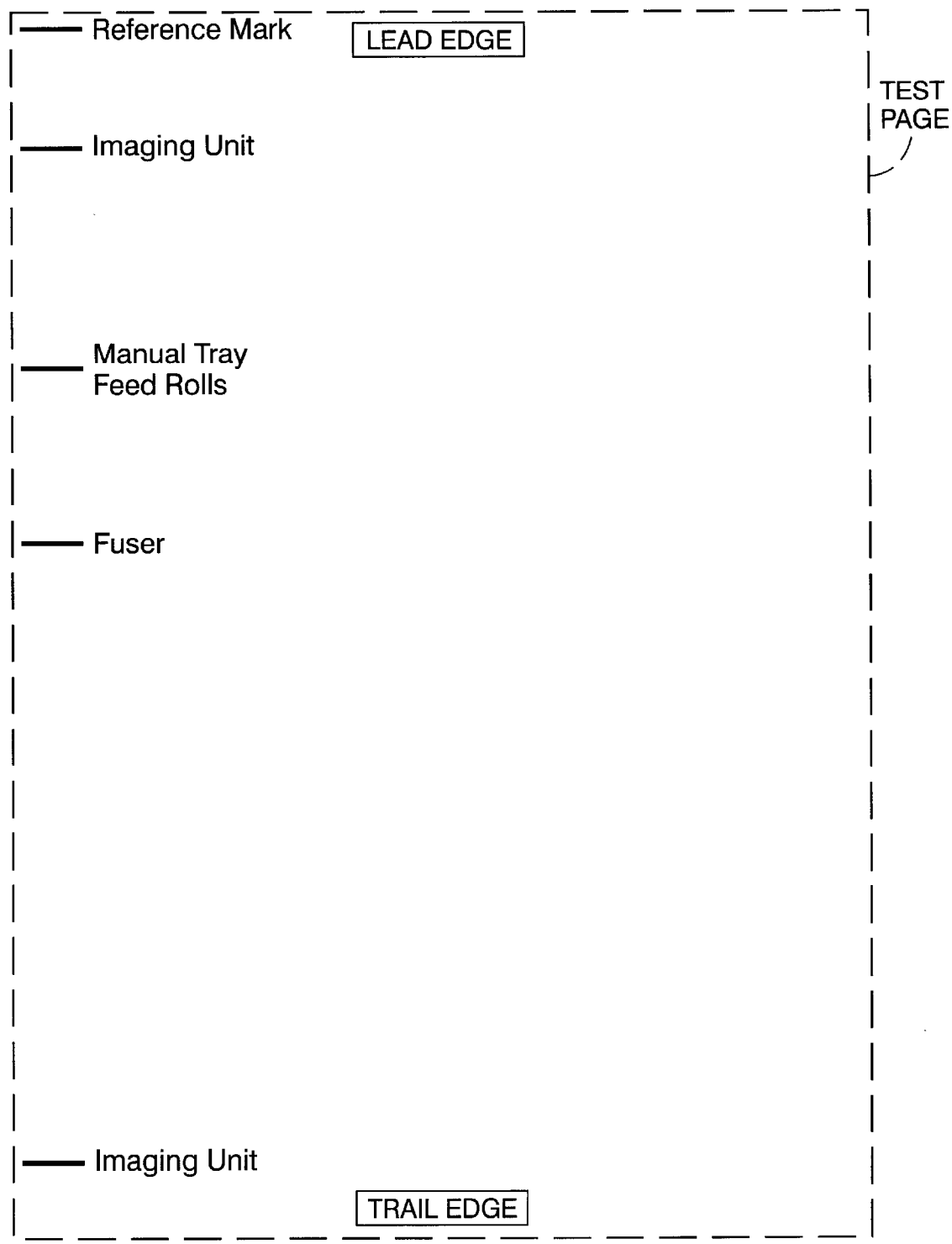

DIAGNOSIS OF REPETITIVE QUALITY FAULTS

BACKGROUND OF THE INVENTION

The present invention relates to printers, and more particularly to a method to improve diagnosis of repetitive quality faults in prints produced by printers having rotating elements.

In printers when certain rotating elements fail they leave a repetitive quality fault in prints. When such a repetitive print quality fault occurs, the user generally calls for a service person to come to the site to diagnose what the cause of the repetitive quality fault is and to repair such fault. This could result in down time for the printer that is not acceptable to the user. The alternative is to replace all of the rotating elements in the hope that the cause of the fault will be cured, or to replace each rotating element one at a time until the fault is cured. This also is time consuming, and may still require a service call if one of the rotating elements is not replaceable by the user.

What is desired is an improved method for diagnosing repetitive quality faults in prints produced by a printer having rotating elements that allows a user to easily diagnose the particular rotating element probably causing the fault, and either replace the element or order a replacement in a timely manner.

BRIEF SUMMARY OF THE INVENTION

Accordingly the present invention provides a method of improving diagnosis of repetitive quality faults appearing in prints produced by printers having rotating elements by providing the printer with an internal test page that has a set of marks along a ruled margin. The mark closest to a lead edge of the test page is a reference mark and characteristic marks are located at a distance from the reference mark along the ruled margin corresponding to the circumference each of the rotating elements that may cause a repetitive quality fault. Each characteristic mark is labeled with the name of the replaceable part associated with the rotating element with that circumference. The test page is printed out and then placed atop the print having the repetitive quality fault. The reference mark is aligned with the first occurrence of the fault and the user observes which characteristic mark aligns with a second occurrence of the fault. The labeling of that characteristic mark indicates the rotating element to be replaced.

The objects, advantages and other novel features of the present invention are apparent from the following detailed description when read in conjunction with the appended claims and attached drawing.

BRIEF DESCRIPTION OF THE SEVERAL VIEWS OF THE DRAWING

The FIGURE is a plan view of an internal test page of a printer for diagnosing repetitive print quality faults according to the present invention.

DETAILED DESCRIPTION OF THE INVENTION

Referring now to the FIGURE an internal test page is shown. The test page may be printed by a printer producing prints having a repetitive quality fault from a front panel menu or remotely over a network to which the printer may be connected. The test page has a lead edge and a trail edge. Along the sides of the test page are a set of test marks that are established for the printer during calibration in the manufacturing process. This test page may include a variety of other test patterns, but only those required for the present invention are shown The first test mark at the lead edge is labeled as a reference mark. The remaining characteristic test marks are spaced from the reference mark along the ruled margin a distance corresponding to the circumference of each rotating element in the printer. For example, if the circumference of a fuser hot roller in a laser printer is four inches, on of the characteristic marks is located approximately four inches from the reference mark. The distances from each characteristic mark to the reference mark may not be exactly equal to the circumference of the rotating element. This is based upon engineering knowledge of image shrinkage, media motion, ratio of rotating element speed to media motion, etc. to determine the exact distances from each characteristic mark to the reference mark. Because of these factors, the distance to the reference mark may not be the same as the circumference of the rotating element. Rotating elements may include rolls or belts in imaging units, manual feed assemblies, fusers, developers, etc.

When a user notices a repetitive quality fault in prints from a printer, the user causes the internal test page to be printed. The user then places the test page atop the print that shows the repetitive quality fault. The user aligns the reference mark with a first occurrence of the repetitive quality fault and observes which of the characteristic marks on the test page aligns with a second occurrence of the fault. The labeling of the characteristic mark that corresponds with the second occurrence of the fault identifies which rotating element probably is causing the fault and needs to be replaced. The user can then replace the identified rotating element, or order a replacement rotating element if not already in the user's possession.

Thus the present invention allows a user to identify a repetitive quality fault in prints from a printer caused by rotating elements in the printer by printing an internal test page having a reference mark and labeled characteristic marks along a ruled margin and aligning the reference mark with the first occurrence of the defect, the characteristic mark next to the second occurrence of the defect identifying the rotating element causing the defect.

What is claimed is:

1. A test page for diagnosing a repetitive quality fault in a print from a printer having rotating elements, the test page being resident in the printer and comprising:

a lead edge and a trail edge;

a ruled margin;

a reference mark at the start of the ruled margin adjacent the lead edge; and characteristic marks along the ruled margin spaced from the reference mark by a distance determined by the circumference of each rotating element in the printer, each characteristic mark having a label identifying a particular one of the rotating elements.

2. A method of diagnosing a repetitive quality fault in a print from a printer having rotating elements comprising the steps of:

printing an internal test page having a lead edge, a trail edge, a ruled margin, a reference mark at the start of the ruled margin adjacent the lead edge, and a plurality of labeled characteristic marks spaced from the reference mark corresponding to circumferences of each of the rotating elements in the printer;

placing the test page atop the print with the reference mark aligned with a first occurrence of the repetitive quality fault; and observing which of the labeled characteristic marks aligns with a second occurrence of the repetitive quality fault, the label for such characteristic mark identifying the rotating element probably causing the repetitive quality fault.

* * * * *